United States Patent
Yim et al.

(10) Patent No.: US 9,364,452 B2
(45) Date of Patent: Jun. 14, 2016

(54) PHARMACEUTICAL COMPOSITION FOR PREVENTING OR TREATING HEPATIC FIBROSIS AND CIRRHOSIS CONTAINING RAMALIN

(75) Inventors: Joung Han Yim, Gyeonggi-do (KR); Il Chan Kim, Seoul (KR); Se Jong Han, Gyeonggi-do (KR); Hyoung Seok Lee, Seoul (KR); Hari Datta Bhattarai, Incheon (KR); Su-Geun Yang, Incheon (KR); Lee Don Hang, Seoul (KR)

(73) Assignee: KOREA INSTITUTE OF OCEAN SCIENCE AND TECHNOLOGY, Gyeonggi-Do (KR)

( * ) Notice: Subject to any disclaimer, the term of this patent is extended or adjusted under 35 U.S.C. 154(b) by 0 days.

(21) Appl. No.: 14/381,490

(22) PCT Filed: Feb. 29, 2012

(86) PCT No.: PCT/KR2012/001519
§ 371 (c)(1),
(2), (4) Date: Sep. 26, 2014

(87) PCT Pub. No.: WO2013/129714
PCT Pub. Date: Sep. 6, 2013

(65) Prior Publication Data
US 2015/0031771 A1    Jan. 29, 2015

(30) Foreign Application Priority Data
Feb. 28, 2012  (KR) .................. 10-2012-0020515

(51) Int. Cl.
A61K 31/165  (2006.01)
A23L 1/30    (2006.01)
A61K 36/09   (2006.01)

(52) U.S. Cl.
CPC ............. *A61K 31/165* (2013.01); *A23L 1/3002* (2013.01); *A61K 36/09* (2013.01); *A23V 2002/00* (2013.01)

(58) Field of Classification Search
CPC .................................................. A61K 31/165
See application file for complete search history.

(56) References Cited

U.S. PATENT DOCUMENTS

| 2010/0086627 A1* | 4/2010 | Zabrecky | A61K 31/198 424/746 |
|---|---|---|---|
| 2011/0262374 A1 | 10/2011 | Yim et al. | |
| 2013/0211133 A1 | 8/2013 | Yim et al. | |

FOREIGN PATENT DOCUMENTS

| KR | 101025612 B1 | 3/2011 |
|---|---|---|
| KR | 10-2011-0132938 A | 12/2011 |

OTHER PUBLICATIONS

Mayo Clinic. "Nutrition and healthy eating". http://www.mayoclinic.org/healthy-lifestyle/nutrition-and-healthy-eating/multimedia/functions-of-water-in-the-body/img-20005799; 2016.*
Huneck, S., "The Significance of Lichens and Their Metabolites", "Naturwissenschaften", Dec. 1999, pp. 559-570, vol. 86.
Ingolfsdottir, K., "Molecules of Interest: Usnic acid", "Phytochemistry", Dec. 2002, pp. 729-736, vol. 61.
Kumar, S., et al, "Lichen Metabolites. 1. Inhibitory Action Against Leukotriene B4 Biosynthesis by a Non-Redox Mechanism", "J. Nat. Prod.", Jun. 1999, pp. 817-820, vol. 62.
Paudel, B., et al., "Ramalin, a novel nontoxic antioxidant compound from the Antarctic lichen *Ramalina terebrata*", "Phytomedicine", Jul. 29, 2011, pp. 1285-1290, vol. 18.
Ahmed, A., "An overview of inflammation: mechanism and consequences", "Frontiers in Biology", Jul. 29, 2011, pp. 274-281, vol. 6, No. 4.
Baber, N., et al., "Indomethacin in rheumatoid arthritis: clinical effects, pharmacokinetics, and platelet studies in responders and nonresponders", "Annals of the Rheumatic Diseases", Apr. 1979, pp. 128-137, vol. 38.
Paudel-Bhattarai, B., "Biology PhD dissertation titled: Isolation and Characterization of Antibacterial and Antioxidant Compounds from the Antarctic Lichen *Ramalina terebrata*", Jan. 2009, pp. I-XVI, 1-138, Publisher: Department of Biology, Graduate School of Soonchunhyang University.
Stanway, A., "The causes of atopic dermatitis (eczema)", Sep. 30, 2015, pp. 1-4, Publisher: DermNetNZ (http://www.dermnetnz.org/dermatitis/atopic-causes.html).
Thaiwat, S., et al., "Omalizumab treatment in severe adult atopic dermatitis", "Asian Pac J Allergy Immunol.", Dec. 2011, pp. 357-360, vol. 29.
Zumla, A., et al., "Tuberculosis", "The New England Journal of Medicine", Feb. 21, 2013, pp. 745-755, supplemental pp. 1-13, vol. 368, No. 8.

* cited by examiner

*Primary Examiner* — Paul Zarek
(74) *Attorney, Agent, or Firm* — Hultquist, PLLC; Steven J. Hultquist

(57) ABSTRACT

There is provided a novel use of ramalin for preventing or treating liver diseases, and more specifically, a pharmaceutical composition for preventing or treating hepatic fibrosis or cirrhosis containing ramalin or a pharmaceutically acceptable salt thereof, and a functional food containing the same. It was confirmed that at the time of applying ramalin, which is a compound derived from *Ramalina terebrata* according to the present invention, to animal models, ramalin may remarkably suppress hepatic fibrosis and lower liver cirrhosis levels as compared to silymarin known as a liver cell protecting ingredient without cytotoxicity to normal liver cells, such that ramalin may be effectively used for preventing or treating hepatic fibrosis and liver cirrhosis.

4 Claims, 9 Drawing Sheets

PHARMACEUTICAL COMPOSITION FOR PREVENTING OR TREATING HEPATIC FIBROSIS AND CIRRHOSIS CONTAINING RAMALIN

CROSS-REFERENCE TO RELATED APPLICATIONS

This application is a U.S. national phase under the provisions of 35 U.S.C. §371of International Patent Application No. PCT/KR12/01519 filed Feb. 29, 2012, which in turn claims priority of Korean Patent Application No. 10-2012-0020515 filed Feb. 28, 2012. The disclosures of such international patent application and Korean priority patent application are hereby incorporated herein by reference in their respective entireties, for all purposes.

TECHNICAL FIELD

The present invention relates to a novel use of ramalin for preventing or treating liver diseases, and more specifically, to a pharmaceutical composition for preventing or treating hepatic fibrosis or liver cirrhosis containing ramalin or a pharmaceutically acceptable salt thereof, and a functional food containing the same.

BACKGROUND ART

It was known that lichens produce unique secondary metabolites different from those of higher plants (Ingolfsdottir, K., *Phytochemistry*, 61:729, 2002), most of the secondary metabolites produced by lichens belong to depside, depsidone, and dibenzfurane, and these compounds are estimated to be associated with a low growth rate of lichens (Kumar, K. C. S. et al., *J. Nat. Prod.*, 62:817, 1999; Huneck, S., *Naturwissenschaften*, 86:559, 1999). In addition, various biological activities including antibiotic, antimicrobactrial, antiviral, analgesic, and antipyretic activities, and the like, were confirmed by a screening process of the metabolites of lichens (Ingolfsdottir, K., *Phytochemistry*, 61:729, 2002; Kumar, K. C. S. et al., *J. Nat. Prod.*, 62:817, 1999). Therefore, the interest in the development of a medicine using the secondary metabolites of lichens has increased.

Meanwhile, the liver is a tissue playing a pivotal role in metabolism of materials from outside the body and materials inside the body. Alcoholic or viral hepatitis develops cirrhosis or liver cancer, but currently, there is no distinct therapeutic material for cirrhosis. Since there are no pains or subjective symptoms in an early stage of hepatic fibrosis, and hepatic fibrosis is found in an end stage, mortality is high, thereby causing social problems. In Northeast Asia and Southeast Asia including China, an expression rate of diseases associated with viral (alcoholic) liver cirrhosis and liver cancer is seriously high. In the case of a therapeutic agent for viral hepatitis, new medicine development has been actively conducted and has been successful in the market, but there is no therapeutic agent for liver cirrhosis except for ursodeoxycholic acid and silymarin. Therefore, in the case of securing a novel material capable of preventing and treating liver cirrhosis, the novel material will be a significant influence on a market in the future.

Therefore, the present inventors have tried to provide a novel material capable of preventing and treating liver cirrhosis and found that ramalin has an effect of preventing and treating hepatic fibrosis and liver cirrhosis in a liver cirrhosis animal model, thereby completing the present invention.

This information disclosed in the present technical field is only to improve understanding of a background of the present invention. Therefore, information on the prior art that is already known by those skilled in the art to which the present invention pertains may not be included.

SUMMARY OF THE INVENTION

An object of the present invention is to provide a novel material capable of preventing and treating liver cirrhosis.

According to an aspect of the present invention, there is provided a pharmaceutical composition for preventing or treating hepatic fibrosis or liver cirrhosis comprising a compound represented by the following Chemical Formula 1 or a pharmaceutically acceptable salt thereof as an active ingredient.

[Chemical Formula 1]

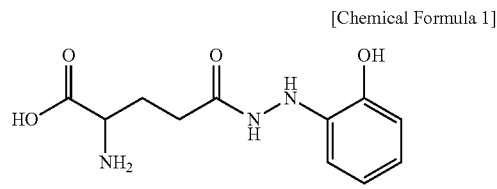 [SMILES: NC(CCC(=O)NNc1ccccc1O)C(=O)O]

According to another aspect of the present invention, there is provided a method of preventing or treating hepatic fibrosis or liver cirrhosis by administering a pharmaceutical composition comprising a compound represented by Chemical Formula 1 or a pharmaceutically acceptable salt thereof as an active ingredient.

According to another aspect of the present invention, there is provided a functional food for preventing or improving hepatic fibrosis or liver cirrhosis comprising a compound represented by Chemical Formula 1 or a sitologically acceptable salt thereof as an active ingredient.

According to another aspect of the present invention, there is provided a method of preventing or improving hepatic fibrosis or liver cirrhosis by administering a functional food comprising a compound represented by Chemical Formula 1 or a cytologically acceptable salt thereof as an active ingredient.

According to another aspect of the present invention, there is provided a pharmaceutical composition for preventing or treating hepatic fibrosis or liver cirrhosis comprising an extract of *Ramalina terebrata* comprising a compound represented by Chemical Formula 1 as an active ingredient.

According to another aspect of the present invention, there is provided a method of preventing or treating hepatic fibrosis or liver cirrhosis by administering a pharmaceutical composition comprising an extract of *Ramalina terebrata* comprising a compound represented by Chemical Formula 1 as an active ingredient.

According to another aspect of the present invention, there is provided a functional food for preventing or improving hepatic fibrosis or liver cirrhosis comprising an extract of *Ramalina terebrata* comprising a compound represented by Chemical Formula 1 as an active ingredient.

According to another aspect of the present invention, there is provided a method of preventing or treating hepatic fibrosis or liver cirrhosis by administering a functional food comprising an extract of *Ramalina terebrata* comprising a compound represented by Chemical Formula 1 as an active ingredient.

Other features and embodiments of the present invention will become obvious from the following detailed description and the accompanying claims.

Figure 1:
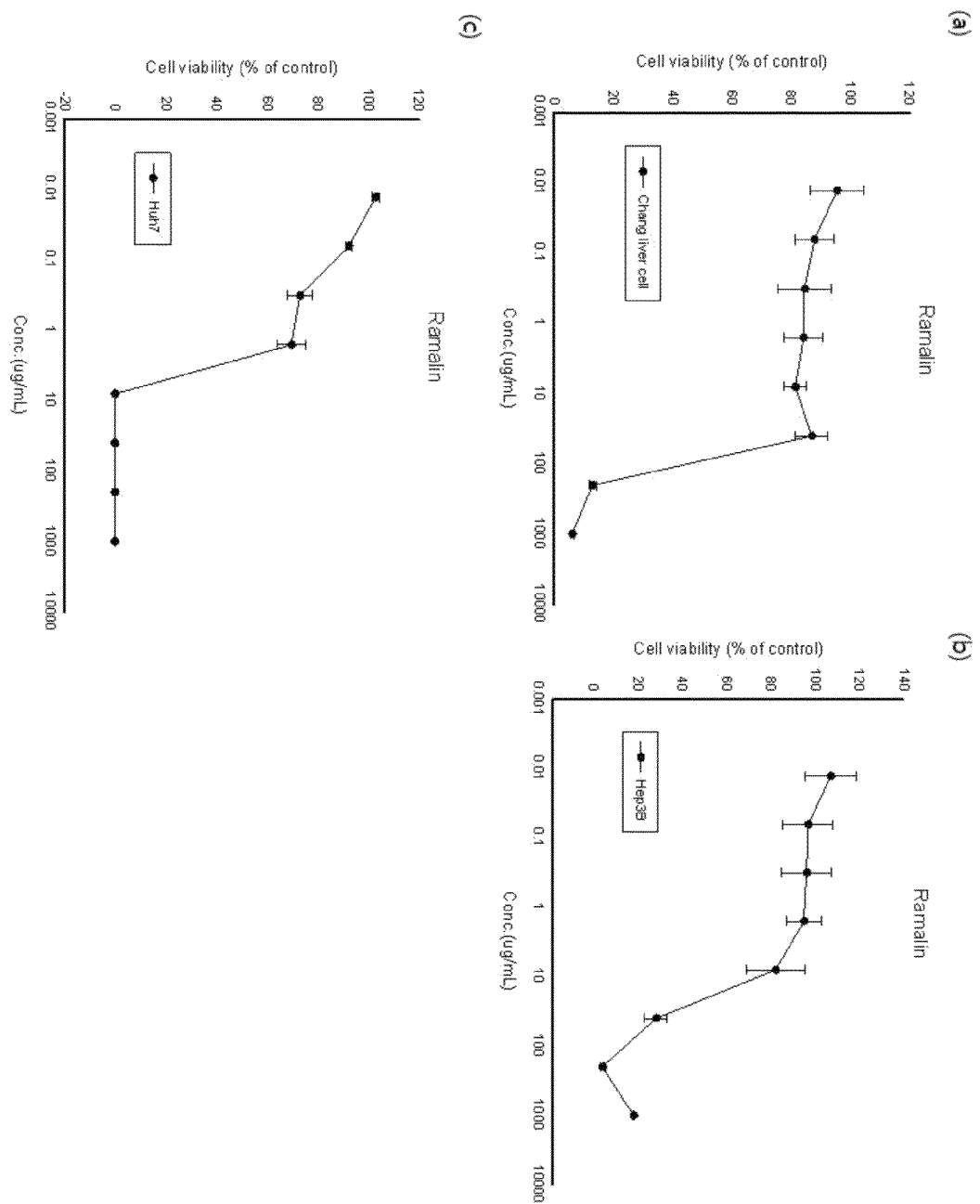
FIGS. 1A to 1C are graphs showing cytotoxicity ($IC_{50}$) measured through cell viability assay at the time of treating liver cancer cell line huh7, Hep3B cells and Chang liver cell with ramalin.

Unless otherwise defined herein, all of the technical and scientific terms used in the present specification have the same meanings as those understood by specialists in the skilled art to which the present invention pertains. Generally, nomenclature used in the present specification is well known and commonly used in the art.

Definitions of main terms used in the detailed description of the present invention are as follows.

The term "liver cirrhosis" as used herein means a disease caused by fibrosis of liver tissues. Here, "hepatic fibrosis" means a state in which a balance in a synthesis and decomposition process of connective tissue is lost, and is caused by excessive accumulation of connective tissue in liver tissue and accompanied with necrosis or inflammation. Particularly, it has been known that hepatic stellate cells (HSCs) serving to store vitamin A in the liver in a state in which hepatic functions are normal are transformed into myofibroblast like cells by acute or chronic liver injury and rapidly proliferated to excessively produce connective tissues by increasing production and movement of extracellular substrates such as collagen, proteoglycan, hyaluronan, and the like, such that a hepatic fibrosis process proceeds.

The term "extract of lichens" as used herein means materials separated by dissolving bodies, tissues, or cells of lichens in a solvent, and the extract may be concentrated by distillation or evaporation.

In an aspect, the present invention provides a pharmaceutical composition for preventing or treating hepatic fibrosis or liver cirrhosis containing a compound represented by the following Chemical Formula 1 or a pharmaceutically acceptable salt thereof as an active ingredient.

[Chemical Formula 1]

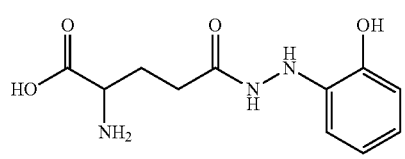

In Example of the present invention, it was confirmed in an experiment for comparing ramalin separated from an extract of *Ramalina terebrata* with silymarin known to have an effect of protecting liver cells in a chronic liver cirrhosis induced animal model that ramalin had an excellent effect of preventing and treating liver cirrhosis and hepatic fibrosis. That is, it was confirmed that in the case in which fibrosis of liver tissue was induced in rat using dimethyl nitrosamine (DMN), AST, ALT, and ALP values indicating liver cirrhosis were significantly increased in serum, and liver cirrhosis was generated due to fibrosis. However, it was confirmed that in a group treated with ramalin, an effect of suppressing hepatic fibrosis was significantly excellent and collagen formation was significantly decreased as compared to a group treated with silymarin, which was a positive control group, and the values indicating liver cirrhosis were also decreased. In addition, an antioxidation effect of ramalin was confirmed by an immunohistological test and a test for confirming protein expression of NADPH quinone oxidoreductase-1 (NQO-1), heme oxygenase-1 (HO-1), and the like, which are genes associated with nuclear erythroid 2-related factor-2 (Nrf-2) and antioxidant response elements (ARE) corresponding to antioxidant indicators.

In addition, ramalin according to the present invention is separated from the extract of *Ramalina terebrata*, and it is apparent that the *Ramalina terebrata* extract itself containing ramalin has the effect of preventing and treating liver cirrhosis and hepatic fibrosis. Therefore, in another aspect, the present invention relates to a pharmaceutical composition for preventing or treating hepatic fibrosis or liver cirrhosis containing the extract of *Ramalina terebrata* including ramalin as an active ingredient.

Meanwhile, Ramalin of Chemical Formula 1, used in the present invention may be in a pharmaceutically acceptable salt form. The pharmaceutically acceptable salt in the present invention may be prepared by a general method used in the art. For example, ramalin may form a pharmaceutically acceptable salt together with an inorganic acid such as hydrochloric acid, hydrogen bromide, sulfuric acid, sodium hydrogen sulfate, phosphoric acid, carbonic acid, or the like, or an organic acid such as formic acid, acetic acid, oxalic acid, benzoic acid, citric acid, tartaric acid, gluconic acid, gentisic acid, fumaric acid, lactobionic acid, salicylic acid, or acetylsalicylic acid (aspirin). In addition, ramalin may react with an alkali metal ion such as a sodium ion or potassium ion to form a metal salt thereof or react with an ammonium ion to form a pharmaceutically acceptable salt in another form.

The pharmaceutical composition containing the compound according to the present invention, the pharmaceutically acceptable salt thereof, or the extract of *Ramalina terebrata* including the compound may be formulated and used in a form for oral administration, such as powders, granules, tablets, capsules, suspensions, emulsions, syrups, aerosols, or the like, for external application, suppository, and sterile injection solutions. As a carrier, an excipient, and a diluent contained in the composition containing the compound, there are lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate, and mineral oil.

In the case in which the pharmaceutical composition is formulated, generally used diluents or excipients such as fillers, extenders, binders, wetting agents, disintegrants, surfactants, or the like, may be used. Solid preparations for oral administration include tablets, pills, powders, granules, capsules, and the like, and may be prepared by mixing the compound with at least one excipient, for example, starch, calcium carbonate, sucrose or lactose, gelatin, or the like. Further, lubricants such as magnesium stearate or talc may be used in addition to simple excipients. Liquid preparations for oral administration include suspensions, solutions, emulsions, syrups, and the like, and various excipients such as a wetting agent, a sweetener, a flavoring agent, a preservant, or the like, as well as water and liquid paraffin that are generally used simple diluents may be contained. Formulations for parenteral administration include sterile aqueous solutions, non-aqueous solvents, suspensions, emulsions, freeze-dried formulations, and suppositories. In the non-aqueous solvent or the suspensions, propylene glycol, polyethylene glycol, vegetable oil such as olive oil, injectable esters such as ethyloleate, or the like, may be used. As a base for suppositories, witepsol, macrogol, tween 60, cacao butter, laurinum, glycerogelatin, or the like, may be used.

In another aspect, the present invention provides a method of preventing or treating hepatic fibrosis or liver cirrhosis by administering a pharmaceutical composition or a functional food comprising a compound represented by the Chemical Formula 1 or a pharmaceutically acceptable salt thereof as an active ingredient.

A preferable dose of the composition according to the present invention may be changed according to a state and weight of a patient, a degree of disease, a drug formulation, and an administration route and duration, but be appropriately selected by those in the art. However, in order to obtain a preferable effect, the compound according to the present invention may be administered at a daily dose of 0.1 to 1,000 mg/kg, preferably 1 to 100 mg/kg. One dose may be administered once a day, or divided into several doses and then administered. The scope of the present invention is not limited to the dose.

As the functional food according to the present invention, for example, there are foods, candies, chocolates, beverages, gums, teas, vitamin complexes, health supplement foods, and the like, and the functional food may be used in a form of powders, granules, tablets, capsules or beverages.

The compound according to the present invention, the sitologically acceptable salt thereof (for example: a sodium salt thereof, or the like), or the extract of *Ramalina terebrata* including the compound may be added to foods or beverages in order to prevent liver cirrhosis or hepatic fibrosis. In this case, a content of the compound in foods or beverages is as follows. In general, a content of the heat functional food composition according to the present invention may be 0.01 to 50 wt %, and preferably 0.1 to 20 wt % based on a total weight of food, and a content of a health beverage composition according to the present invention may be 0.02 to 10 g, and preferably 0.3 to 1 g, based on 100 ml of the health beverage.

There is no particular limitation in liquid components of the health beverage composition according to the present invention as long as the health beverage composition contains the compound according to the present invention as an essential ingredient at the ratio as described, and the health beverage composition may further contain various flavors, natural carbohydrates, or the like, as additional ingredients, similarly to general beverages. Examples of the natural carbohydrates include general sugars, for example, monosaccharide such as glucose, fructose, and the like, disaccharides such as maltose, sucrose, and the like, and polysaccharides such as dextrin, cyclodextrin, and the like, and sugar alcohols such as xylitol, sorbitol, erythritol, and the like. As the flavor, natural flavors (thaumatin, stevia extracts (for example, rebaudioside A, glycyrrhizin, and the like) and synthetic flavors (saccharine, aspartame, and the like) may be advantageously used. The content of the natural carbohydrate in the composition according to the present invention is about 1 to 20 g, and preferably about 5 to 15 g, based on 100 ml of the composition. Besides the additional ingredients as described above, the functional food according to the present invention may contain various nutrients, vitamins, minerals (electrolytes), flavorants such as synthetic flavorants and natural flavorants, colorants and improving agents (cheese, chocolate, and the like), pectic acid and salts thereof, alginic acid and salts thereof, organic acids, protective colloid thickeners, pH control agents, stabilizers, preservatives, glycerin, alcohols, carbonating agents used in a carbonated beverage, or the like. In addition, the functional food according to the present invention may contain fruit flesh for preparing natural fruit juices, fruit juice beverages, and vegetable beverages. These ingredients may be used independently or in combination. Although the content of these additives is not particularly important, is generally selected in a range of 0 to 20 parts by weight based on 100 parts by weight of the composition according to the present invention.

Hereinafter, the present invention will be described in detail through the Examples. However, these Examples are only to illustrate the present invention, and those skilled in the art will appreciate that these Examples are not to be construed as limiting a scope of the present invention.

EXAMPLES

Example 1

Separation of *Ramalin*

1-1: Preparation of Extract of *Ramalina terebrata* and Separation of *Ramalin*

*Ramalina terebrata*, which is a lichen strain naturally growing in groups in King George Island, Antarctica, may be collected from King George 672 g of a completely freeze-dried and ground lichen *Ramalina terebrata* sample was repeatedly extracted with a mixed solution of methanol and water (5 L, 80:20v/v) three times, and then freeze-dried, thereby obtaining 83 g of a crude extract. The crude extract was dissolved in 1 L of distilled water and extracted with 1 L of n-hexane and chloroform (CHCl$_3$), thereby obtaining 12.7 g of n-hexane, 9.1 g of chloroform (CHCl$_3$), and 61.0 g of a water-soluble extract. The water-soluble extract showed a high activity (IC$_{50}$=9 ug/ml) against 2,2-diphenyl-1-picryl-hydrazyl-hydrate (DPPH). A portion (5 g) of the water-soluble extract was subjected to automatized mild pressure liquid chromatography (MPLC) using a stepwise gradient solvent system of 0%, 20%, 40%, 60%, 80% and 100% methanol in water solutions. The extract eluted in 0% methanol in water solution showed a high activity (IC$_{50}$=8 ug/ml) against a DPPH free radical, and a portion (100 mg) thereof was analyzed by semi-preparative reverse phase HPLC using a C$_{18}$ODS column (250 cm×10 cm). The used solvent system was 0% methanol in water containing 0.1% formic acid (over 10 min), 20% methanol (over 20 min), and 100% methanol (over 30 min). A flow rate was 2 mL/min and detection was performed at 280 nm.

As a result, the fifth fraction (45 mg; t$_R$=18.88 min) showed a highest activity (IC$_{50}$=1 µg/ml) against the DPPH free radicals, and this fraction was repeatedly purified by semi-preparative reverse phase HPLC using a C18ODS column (250 cm×10 cm). The gradient solvent system was 10-30% acetonitrile in water containing 0.1% formic acid (over 50 min), and a flow rate was 2 mL/min. As a result, 30 mg of ramalin of the following Chemical Formula 1, of which an activity against the DPPH free radical activity is IC$_{50}$=0.99 µg/mL, was obtained at 8.26 min.

[Chemical Formula 1]

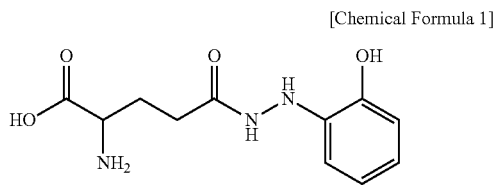 [SMILES: NC(CCC(=O)NNc1ccccc1O)C(=O)O]

Example 2

Cytotoxicity Evaluation

Cytotoxicity evaluation of ramalin was confirmed using huh7 and Hep3B cells (Korean Cell Line Bank, Korea), which are liver cancer cell lines, and Chang liver cell, (ATCC, USA), which is a normal liver cell. That is, Hep3B cell and Huh7 cell were seeded, cultured in a 96-well plate for 24 hours, and then treated with ramalin according to the predetermined concentrations. After culturing the cells for 3 days, a medium was removed, and the cells were washed with the medium. Then, cytotoxicity (IC$_{50}$) was measured by cell viability assay. Cytotoxicity (IC$_{50}$) was measured in the normal liver cell (Human Change liver cell) by cell viability assay using the same method as described above.

TABLE 1

| Cell Line | IC$_{50}$ (ug/mL) |
|---|---|
| Chang liver cell | 118.30 |
| Hep 3B | 23.77 |
| Huh 7 | 2.11 |

As a result of the cytotoxicity of ramalin, the IC$_{50}$ values were 23.77 ug/mL and 2.11 ug/mL in the Hep3B and Huh7 cells, which are liver cancer cell lines, and in Chang liver cell (normal liver cell), the IC$_{50}$ value was 118.3 ug/mL as shown in Table 1 and FIG. 1, such that ramalin acted specifically on liver cancer cell lines, and there was almost no toxicity in the normal liver cell line.

Example 3

Effect Test in Disease Animal Model 3-1: Establishment of Chronic Liver Cirrhosis Animal Model In order to establish a chronic liver cirrhosis animal model, 8-weeks old SD rats (Orientbio Inc., Gapyenong Center, Korea) were used after an acclimation period, and 1% dimethyl nitrosamine (DMN) was i.p. injected at a dose of 1 mL/kg body weight three times a week (Monday, Tuesday, and Wednesday) for 4 weeks (28 days), thereby establishing a chronic liver cirrhosis model.

3-2: Configuration of Test Groups

The entire number of test groups was 6, and more specifically, the test groups were configured as follows.

1) In a control group, any material was not administered (n=6), or MCT-oil was administered to the others (n=3).

2) In a ramalin (RM) group, ramalin was administered at 20 mg/kg three times a week (Monday, Wednesday, and Friday) (n=8).

3) In a silymarin (SM) group, silymarin (Sigma Aldrich) was administered at 100 mg/kg three times a week (Monday, Wednesday, and Friday) (n=6).

4) In a DMN group, 1% dimethyl nitrosamine (DMN) was i.p.-injected at a dose of 1 mL/kg body weight three times a week (Monday, Tuesday, and Wednesday) for 4 weeks (28 days).

5) In a RMDM group, 1% dimethyl nitrosamine (DMN) was i.p.-injected at a dose of 1 mL/kg body weight three times a week (Monday, Tuesday, and Wednesday) for 4 weeks, and at the same time, ramalin was administered at 20 mg/kg three times a week (Monday, Wednesday, and Friday).

6) In a SMDM group, 1% dimethyl nitrosamine (DMN) was i.p.-injected at a dose of 1 mL/kg body weight three times a week (Monday, Tuesday, and Wednesday) for 4 weeks, and at the same time, silymarin was administered at 100 mg/kg three times a week (Monday, Wednesday, and Friday).

In this case, ramalin was prepared by being dissolved in drinking water at 20 mg/kg immediately before administration, and directly, the prepared ramalin was orally administered, and silymarin corresponding to a positive control group was prepared by being dissolved in MCT oil at 100 mg/kg immediately before administration, and directly, the prepared silymarin was orally administered.

3-3: Observation of Death and Clinical Symptom and Measurement of Body Weight and Liver Weight First, whether or not the animal was died or dying was observed and clinical symptoms of the animal were observed during an administration period and up to a blood collecting termination time in all animals. As a result, during the test, in the control group, the RM group, the SM group, and the RMDM group, died or dying animals were not observed, but in the DMN and SMDM groups, died or dying animals were observed (respectively, n=1).

Figure 2:
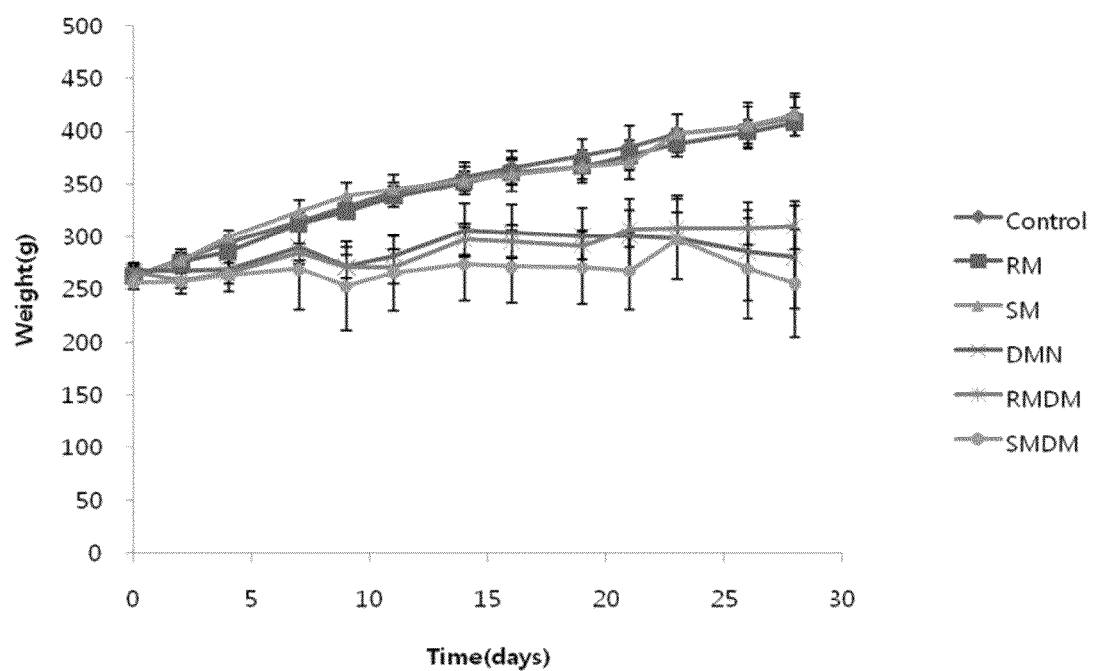
FIG. 2 is a graph showing a result of measuring weight changes before administration and during an administration period of each material in a control group, a RM group, a SM group, a DMN group, a RMDM group, and a SMDM group.

Additionally, after the acclimation period, body weights were measured immediately before administration, and after separating the animals into the groups, body weights were measured 2 to 3 times a week. As a result, in the RM and SM groups, the body weight was not decreased, but increased similarly to the control group as shown in FIG. 2. However, in the DMN treated groups (DMN group, RMDM group, and SMDM group), a weight increase rate was significantly low as compared to the DMN non-treated groups. In the DMN group, the body weight was decreased by 32%, in the RMDM group, the body weight was decreased by 25%, and in the SMDM group, and the body weight was decreased by 38%, as compared to the control group.

Figure 3:
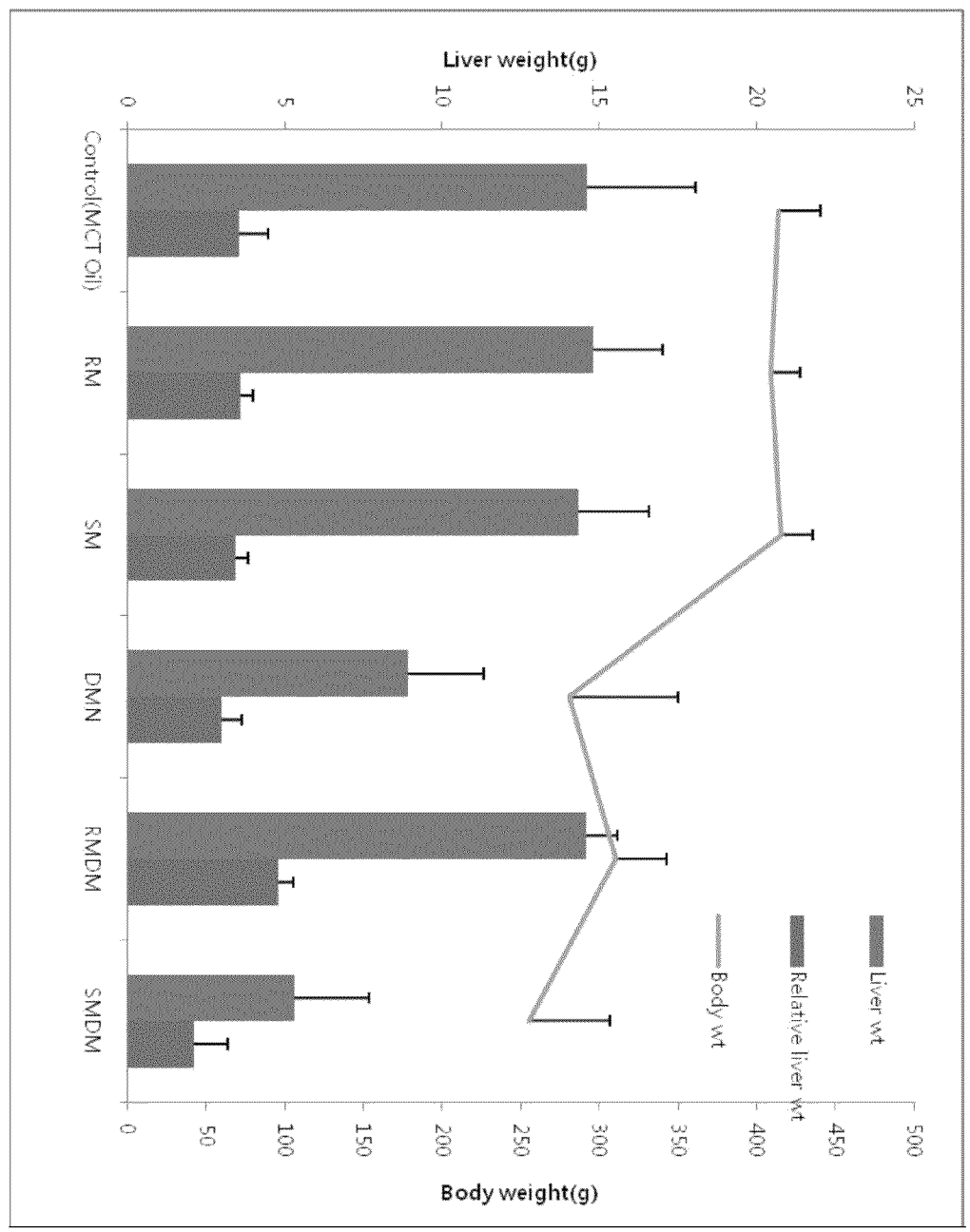
FIG. 3 is a graph showing a result of measuring a liver weight and calculating a relative liver weight to a body weight in the control group, the RM group, the SM group, the DMN group, the RMDM group, and the SMDM group after termination of an experiment.

Further, after termination of an experiment, the liver was extracted and washed with phosphate buffered saline (PBS) to remove blood clot. Then, the weight was measured, and a relative liver weight to the body weight was calculated. As a result, in the DMN and SMDN groups, the relative liver weight after termination of the experiments to the body weight was low, and in the RMDM group, the relative liver weight to the body weight was similar to that in the control group as shown in FIG. 3.

3-4: Blood Biochemical Test

After termination of administration, the animals were anesthetized, and blood was collected from each of the animals and centrifuged at 4° C. 3,000 rpm for 10 min, such that a supernatant serum was collected and used as a sample. Almandine transaminase (ALT), aspartate transminase (AST), albumin, total protein, alkaline phosphate (ALP), total bilirubin (T-bilirubin), direct bilirubin (D-bilirubin), and the like, in the serum sample were measured by Samkwang Medical Laboratories.

Figure 4:
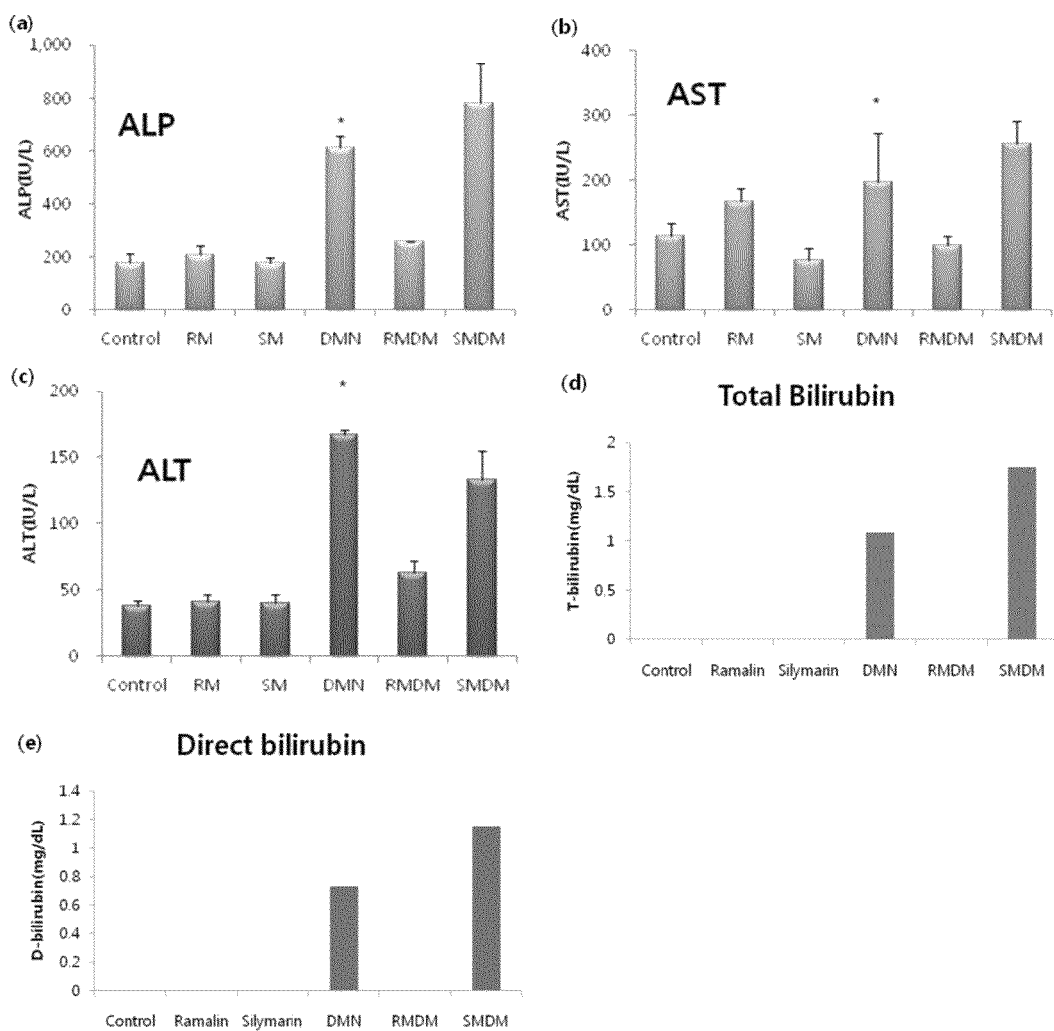
FIG. 4 is a graph showing a result of performing a blood biochemical test in the control group, the RM group, the SM group, the DMN group, the RMDM group, and the SMDM group after termination of the experiment.

As a result, it was confirmed that in this group, T-Bilirubin, D-Bilirubin, ALP, AST, and ALT values were significantly increased (two times or more the normal values) as shown in FIG. 4, such that liver cirrhosis occurred in the DMN group, and in the RM and SM groups in which DMN was not administered, the result was similar to that in the control group. It was confirmed that in the RMDM group, the ALT value was increased about 1.5 times the normal value, but was significantly low as compared to the DMN group. In the SMDM group, values similar to those in the DMN group were obtained.

3-5: Confirmation of Whether or not Fibrosis is Formed by MT Staining

After termination of administration, the animals were anesthetized, and liver tissue was extracted from each of the animals. Then, a weight of the liver tissue was measured and photographed, and then the tissue was fixed to 10% buffered neutral formalin. The fixed tissue was trimmed at a predetermined thickness, subjected to a general tissue treatment process, and embedded in paraffin, thereby preparing a tissue section (4~5 μm). Thereafter, in order to observe fibrosis occurred at the time of liver cirrhosis, a Masson's trichrome (MT) staining was performed, such that a degree of fibrosis was confirmed, and it was confirmed that at the time of administering ramalin, fibrosis was decreased.

Figure 5:
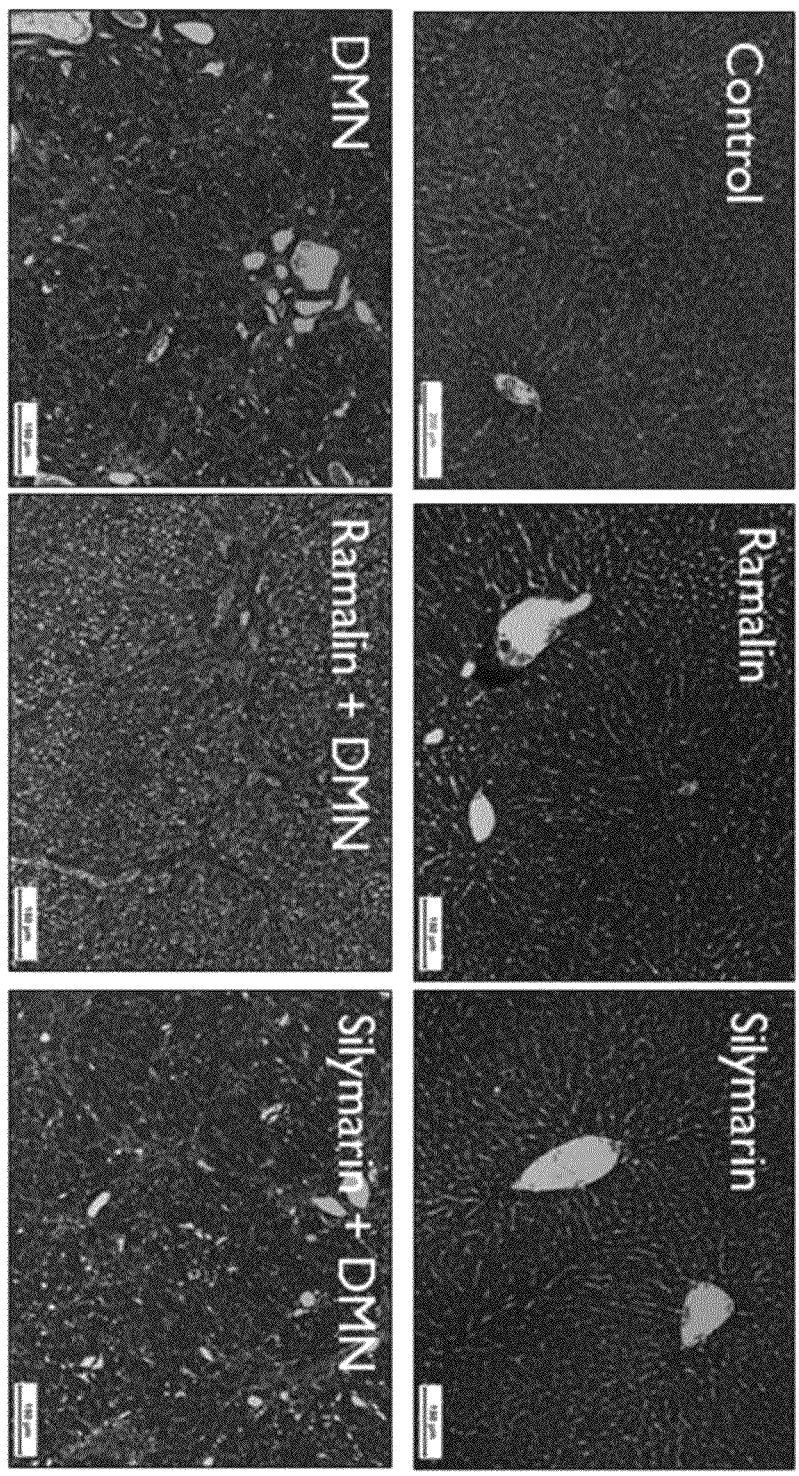
FIG. 5 is a graph showing a result of performing MT staining in the control group, the RM group, the SM group, the DMN group, the RMDM group, and the SMDM group after termination of the experiment.

As a result, it was confirmed that in the DMN treated group (the DMN group, the RMDM group, and SMDM group), fibrosis sites were stained in blue color in a net shape and a large amount of collagen was formed as shown in FIG. 5. However, in the RMDM group, fibrosis formation was significantly decreased as compared to the DMN and SMDM groups.

3-6: Analysis of Hydroxyproline

In order to measure an amount of collagen in the tissue, a hydroxyproline, which is an ingredient of collagen, was measured. 1 ml of 6M HCl was added to 100 mg of liver tissue extracted in the experimental Examples and homogenized, and then boiled at 120° C. for 20 min. The resultant was centrifuged, and a supernatant was collected and concentrated at 50° C. for 36 to 48 hours. After 1 mM HCl was added thereto to disperse the concentrated resultant again, the dispersed resultant was centrifuged and 50 uL of a supernatant was collected. 450 uL of chloramine T solution was added thereto and an oxidation reaction was performed for 25 min, and then Ehrich's reagent was added thereto and reacted at 65° C. for 20 min. Thereafter, UV absorbance was measured at 558 nm.

Figure 6:
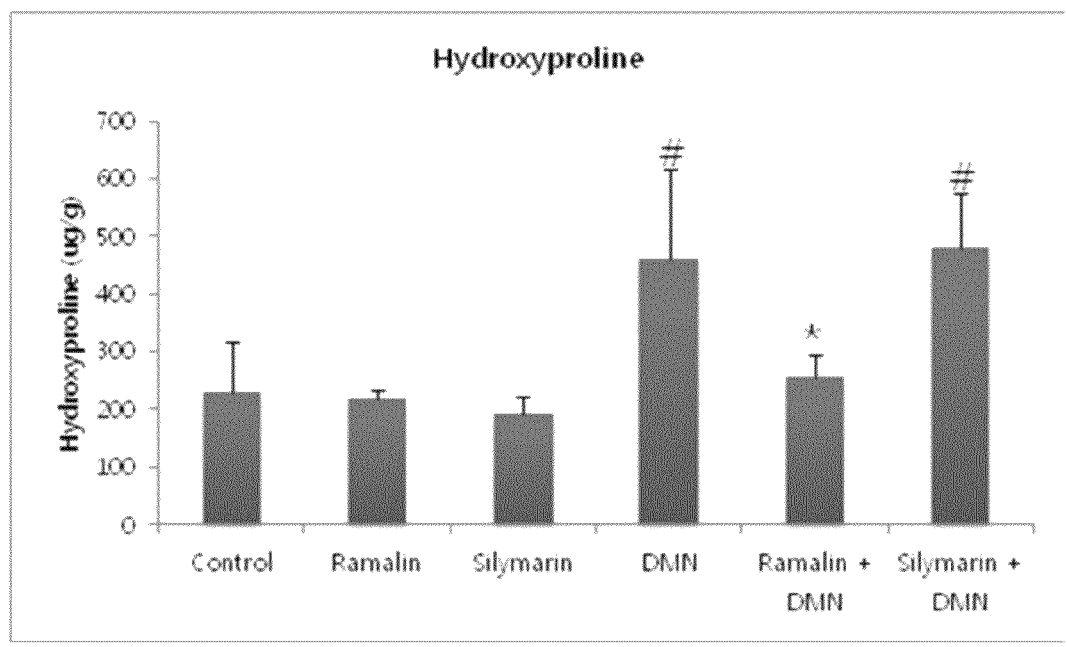
FIG. 6 is a graph showing a detection amount of hydroxyproline, which is an ingredient of collagen, in the control group, the RM group, the SM group, the DMN group, the RMDM group, and the SMDM group after termination of the experiment.

As a result, in the RMDM group, an amount of hydroxyproline was significantly low as compared to the DMN group as shown in FIG. 6. The result means that a small amount of collagen was formed. It was confirmed that in the RM and SM groups, the amount of hydroxyproline was similar to than in the control group.

3-7: Immunohistochemical Test

After preparing a paraffin section by slicing a paraffin block at a thickness of 4 and drying the sliced paraffin block, deparaffinization was performed using an organic solvent (here, Histosolve, ThermoShandon). Endogenous peroxidase existing in the tissue was suppressed by a reagent obtained by adding hydrogen peroxide to ethanol, and endogenous alkaline phosphatase was suppressed by acidic alcohol. A protein blocking solution was used in order to suppress proteins capable of non-specifically binding to a primary antibody. After treating the primary antibody, the washing was performed using phosphate buffered saline (PBS, pH 7.4) solution, and after treating a secondary antibody, the PBS solution was also used for washing. In the primary antibody test, Nrf-2(1:200, Santa Cruz Biotechnology, USA), NQO-1 (1 μg/mL, Abcam, UK), and HO-1 (1:250, Enzo Life Science, USA) were tested, similarly to a protein test using a Western blot method.

Figure 7:
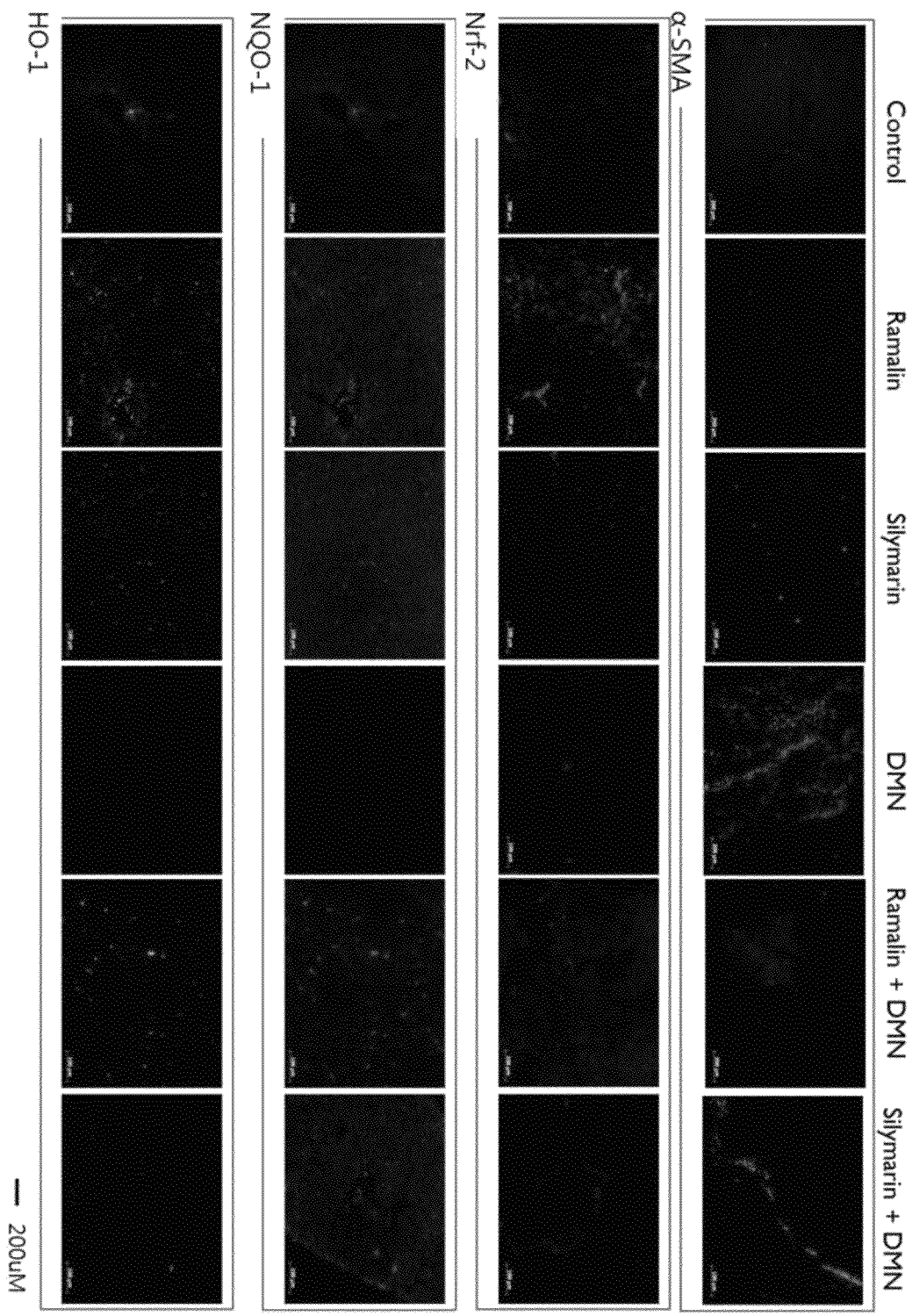
FIG. 7 is photographs for confirming expression amounts of α-SMA, Nrf-2, NQO-1, and HO-1 in the control group, the RM group, the SM group, the DMN group, the RMDM group, and the SMDM group after termination of the experiment.

As a result, at the time of an increase in hepatic fibrosis, an expression amount of α-SMA was high as shown in FIG. 7, and as a result of the liver tissue staining, in the DMN group, the expression amount was highest. In the RMDM group, the expression amount of α-SMA was smaller than that in the DMN group. Nrf-2, which is an antioxidant indicator, was expressed in the RM and SM groups, and Nrf-2 was hardly expressed in the DMN and SMDM groups. In the RMDM group, expression of Nrf-2 was confirmed. As a result of confirming expression of NQO-1 and HO-1, which are ARE-bearing genes, NQO-1 was highly expressed in the RM, SM, RMDM, and SMDM groups, and HO-1 was expressed in the RM and RMDM groups.

3-8: Confirmation of mRNA Expression of Interleukin (IL)-6, TNF-α, and Interleukin-4 in Liver Tissue Expression of IL-6, TNF-α, and IL-4, which are signaling molecules mediating an inflammatory response, was confirmed at an mRNA level. The crushed live tissue was collected, and RNA was separated therefrom using Trizol (invitrogen) and transcripted into a reverse transcription system (Promega). Then, expression of IL-6, IL-4, and TNF-α was confirmed using a polymerase reaction (PCR), and GAPDH was used as a control group.

Figure 8:
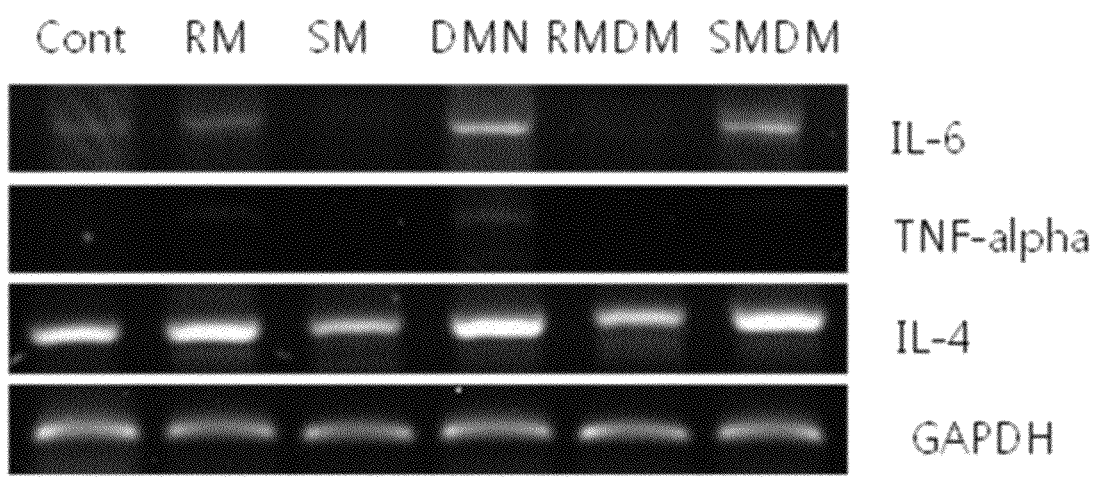
FIG. 8 is an electrophoresis photograph for confirming whether or not interleukin-6, TNF-α, interleukin-4 mRNA are expressed in the control group, the RM group, the SM group, the DMN group, the RMDM group, and the SMDM group after termination of the experiment.

As a result, it was confirmed that in the DMN group, expression of IL-4, IL-6, and TNF-α was increased, and in the RMDM group, expression thereof was decreased as shown in FIG. 8.

3-9: Confirmation of Expression Amount of Antioxidant Enzymes and α-SMA in Liver Tissue After termination of the experiment, the crushed liver tissue was collected, and protein was extracted using an extraction buffer and quantified. Then, expression of antioxidant enzymes was confirmed by western blot. An amount of the protein was 40 ug, and beta-actin was used as a control group.

Figure 9:
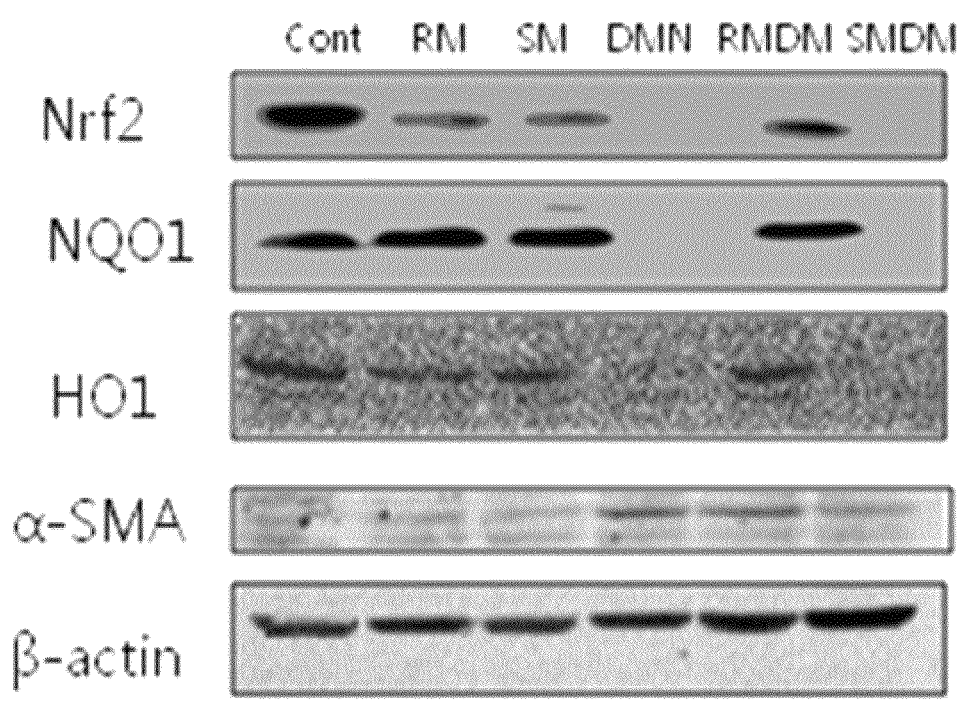
FIG. 9 is an electrophoresis photograph for confirming whether or not Nrf-2, NQO-1, HO-1, α-SMA, beta-actin are expressed in the control group, the RM group, the SM group, the DMN group, the RMDM group, and the SMDM group after termination of the experiment.

As a result, expression of Nrf-2, which is the antioxidant indicator and NQO-1 and HO-1, which are ARE-bearing genes, was confirmed at a protein level as shown in FIG. 9. Nrf-2, NQO-1, and HO-1 were not expressed in the DMN and SDMD groups, but expression of Nrf-2, NQO-1, and HO-1 was confirmed in the RMDM group. Expression of α-SMA was confirmed in all of the DMN, RMDM, and SMDM groups. There is no significant difference between the RM and SM groups and the control group.

According to Lee-CG, et al, (Lee-CG et al., Gastroenterology, DOI: http://dx.doi.org/10.1053/j.gastro.2012.01.007), it was known that micro-RNA called miR-199a-3p suppresses LKB1 involved in antioxidation and anti-cancer mechanism of liver cells to damage liver cells. The experimental results as described above show that ramalin according to the present invention has an effect of preventing and treating hepatic fibrosis and liver cirrhosis.

INDUSTRIAL APPLICABILITY

As set forth above, it was confirmed that at the time of applying ramalin, which is compound derived from *Ramalina terebrata* according to the present invention, to animal models, ramalin may remarkably suppress hepatic fibrosis and lower liver cirrhosis levels as compared to silymarin known as liver cell protecting ingredient without cytotoxicity to normal liver cells, such that ramalin may be effectively used for preventing or treating hepatic fibrosis and liver cirrhosis.

Although the present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

What is claimed is:

1. A method of treating hepatic fibrosis or liver cirrhosis, comprising administering a pharmaceutical composition in which active ingredient effective for such treating consists of a compound represented by a following Chemical Formula 1 or a pharmaceutically acceptable salt thereof:

[Chemical Formula 1]

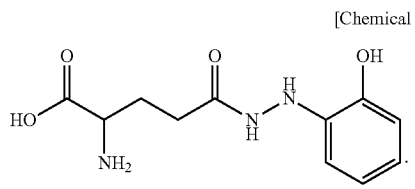

2. A method of improving hepatic fibrosis or liver cirrhosis, comprising administering a functional food in which active ingredient effective for such treating consists of a compound represented by a following Chemical Formula 1 or a cytologically acceptable salt thereof:

[Chemical Formula 1]

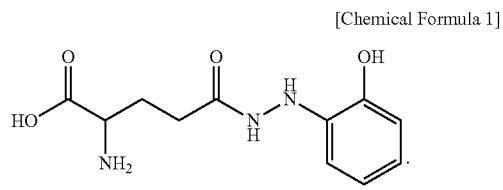 [SMILES: NC(CCC(=O)NNc1ccccc1O)C(=O)O]

3. A method of treating hepatic fibrosis or liver cirrhosis, comprising administering a pharmaceutical composition in which active ingredient effective for such treating consists of an extract of *Ramalina terebrata* comprising a compound represented by a following Chemical Formula 1:

[Chemical Formula 1]

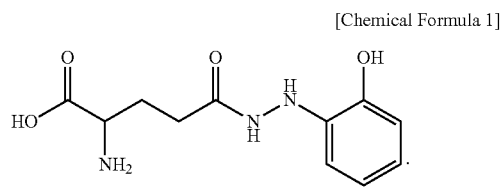

4. A method of improving hepatic fibrosis or liver cirrhosis, comprising administering a functional food in which active ingredient effective for such improving consists of an extract of *Ramalina terebrata* comprising a compound represented by a following Chemical Formula 1:

[Chemical Formula 1]

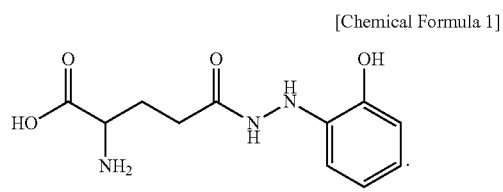 [SMILES: NC(CCC(=O)NNc1ccccc1O)C(=O)O]

* * * * *

UNITED STATES PATENT AND TRADEMARK OFFICE
CERTIFICATE OF CORRECTION

PATENT NO.       : 9,364,452 B2
APPLICATION NO.  : 14/381490
DATED            : June 14, 2016
INVENTOR(S)      : Joung Han Yim et al.

It is certified that error appears in the above-identified patent and that said Letters Patent is hereby corrected as shown below:

IN THE SPECIFICATION

Column 6, line 42: "important, is generally" should be -- important, it is generally --.

Column 6, line 61: "King George" should be -- King George Island. --.

Column 11, line 17: "which is compound" should be -- which is a compound --.

Column 11, lines 20-21: "known as liver" should be -- known as a liver --.

Signed and Sealed this
Ninth Day of August, 2016

Michelle K. Lee
*Director of the United States Patent and Trademark Office*